United States Patent

Bromfield et al.

[11] Patent Number: 5,879,364
[45] Date of Patent: Mar. 9, 1999

[54] INTERNAL ULTRASONIC TIP AMPLIFIER

[75] Inventors: George Bromfield, Murray, Utah; Jeffrey J. Vaitekunas, West Chester, Ohio

[73] Assignee: Ethicon Endo-Surgery, Inc., Cincinnati, Ohio

[21] Appl. No.: 941,554

[22] Filed: Sep. 30, 1997

Related U.S. Application Data

[62] Division of Ser. No. 657,146, Jun. 3, 1996, Pat. No. 5,746,756.

[51] Int. Cl.$^6$ ............................................. A61B 17/32
[52] U.S. Cl. ................................... 606/169; 604/22
[58] Field of Search ............................. 606/159, 170, 606/167, 180, 169; 604/22, 164, 158

[56] References Cited

U.S. PATENT DOCUMENTS

| | | | |
|---|---|---|---|
| 2,704,333 | 3/1955 | Calosi et al. ........................... | 601/2 |
| 4,870,953 | 10/1989 | Donmichael et al. . | |
| 4,897,079 | 1/1990 | Zaleski et al. . | |
| 4,931,047 | 6/1990 | Broadwin et al. . | |
| 4,979,952 | 12/1990 | Kubota et al. . | |
| 5,011,471 | 4/1991 | Miyazaki et al. . | |
| 5,026,387 | 6/1991 | Thomas . | |
| 5,123,903 | 6/1992 | Ureche . | |
| 5,160,317 | 11/1992 | Costin . | |
| 5,180,363 | 1/1993 | Idemoto et al. . | |
| 5,190,517 | 3/1993 | Zieve et al. . | |
| 5,236,414 | 8/1993 | Takasu ................................. | 604/22 |
| 5,344,420 | 9/1994 | Hilal et al. . | |
| 5,417,672 | 5/1995 | Nita et al. . | |
| 5,449,370 | 9/1995 | Vaitekunas . | |
| 5,472,447 | 12/1995 | Abrams et al. . | |
| 5,514,087 | 5/1996 | Jones ................................... | 604/22 |

FOREIGN PATENT DOCUMENTS

| | | |
|---|---|---|
| 10998003 | 3/1981 | Canada . |
| 61-265136 | 5/1985 | Japan . |
| 1388002 | 4/1988 | U.S.S.R. . |

OTHER PUBLICATIONS

Hilal et al., Surgical Trocar, PCT Application, Int'l Publication Date: 03 Sep. 1992, Int'l Publication No. WO 92/14514.

Vaitekunas, Jeffrey J., Blunt Tipped Ultrasonic Trocar, EPO Application, Date of Publication: 17 Nov. 1994, Publication No. 0 624 346 A2.

*Primary Examiner*—Gary Jackson
*Assistant Examiner*—Kevin Truong

[57] ABSTRACT

An ultrasonic energy amplifier. The amplifier comprises a delivery horn having a solid proximal portion and a hollow distal portion. The hollow distal portion has substantially less cross-sectional area than the solid proximal portion. Ultrasonic energy is transmitted sequentially through the proximal and distal portions and its velocity is amplified because of the lower cross-sectional area of the distal portion.

38 Claims, 2 Drawing Sheets

5,879,364

INTERNAL ULTRASONIC TIP AMPLIFIER

This application is a division of application Ser. No. 08/657,146, filed Jun. 3, 1996 now U.S. Pat. No. 5,746,756.

BACKGROUND OF THE INVENTION

1. The Field of the Invention

The present invention relates generally to penetration and dissolution devices. More particularly, it concerns a hollow amplifying tip for amplifying the velocity of ultrasonic energy produced by an ultrasonic transducer and delivering the energy to a subject to be penetrated or modified.

2. The Background Art

Modern surgery involves the insertion of various surgical tools into a patient, which requires incisions to be made in the patient. It is known in medical technology to create an artificial access to body cavities and organs within the patient which do not posses any natural communicating passage to the patient's exterior. Cannulation instruments known as trocars have been used for this purpose.

For example, in endoscopic surgery a sharp-pointed trocar removably surrounded by a sleeve is used to penetrate the peritoneum. The trocar pierces the body tissue and widens the opening to the diameter of the sleeve. The sleeve is pushed into the opening and the trocar is removed from the sleeve. The sleeve remains lodged in the opening to serve as a passageway through which endoscopes and other surgical tools can be inserted and removed.

The insertion of the trocar, even with the advantageous selection of an injection site, involves the risks of inadvertently damaging delicate internal organs and blood vessels in the peritoneum and surrounding fatty tissues. There is also the risk after penetration that organs and blood vessels within the abdominal cavity can be damaged by further movement of the trocar.

Attempts have been made in the prior art to solve these problems. For example, U.S. Pat. No. 5,271,380 (issued Dec. 21, 1993 to Riek et al.) discloses a penetration instrument which includes optical fibers used to illuminate the organs and blood vessels to the view of the surgeon. This device attempts to provide observation of the area lying directly in front of the sharp-pointed trocar, to avoid inadvertent damage to the organs and blood vessels. In this application as well, however, piercing the peritoneum with a sharp-pointed object remains the central method of penetration, and thus the risk of damage during insertion of the trocar remains.

OBJECTS AND SUMMARY OF THE INVENTION

It is therefore an object of the present invention to provide an apparatus for penetrating human tissue which is blunt ended.

It is another object of the invention to provide such an apparatus which is useable as part of an ultrasonic transducing device.

It is a further object of the invention to provide such an apparatus which is capable of amplifying the velocity of ultrasonic energy without a reduction in external dimensions of the apparatus.

It is an additional object of the present invention, in accordance with one aspect thereof, to provide such an apparatus which is more efficient in amplifying velocity of ultrasonic energy.

It is also an object of the present invention to propagate ultrasonic energy through a hollow tip to thereby amplify the velocity of the ultrasonic energy.

The above objects and others not specifically recited are realized in a specific illustrative embodiment of an ultrasonic energy amplifier. The amplifier comprises a delivery horn having a solid proximal portion and a hollow distal portion. The hollow distal portion has substantially less cross-sectional area than the solid proximal portion. Ultrasonic energy is transmitted sequentially through the proximal and distal portions and its velocity is amplified because of the lower cross-sectional area of the distal portion.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION OF PRESENTLY PREFERRED EMBODIMENTS

Figure 1A:
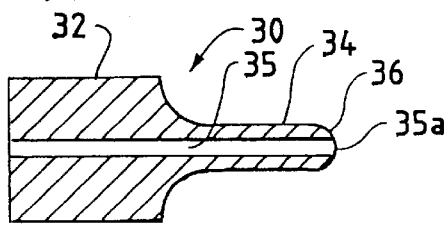
FIG. 1A is a side, cross-sectional view of a prior art ultrasonic tip amplifier.

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and further modifications of the illustrated apparatus, and any additional applications of the principles of the invention as illustrated herein, which would normally occur to one skilled in the relevant art and possessed of this disclosure, are to be considered within the scope of the invention claimed.

Applicants have discovered that human tissue can be more effectively and safely penetrated without the sharp-pointed trocars of the prior art, by using ultrasonic energy amplified by a hollow delivery horn. The hollow delivery horn provides the advantages of optimal amplification of ultrasonic energy without narrowing the external dimensions of the horn necessarily. Further, the applications of the present invention are not limited to replacing the trocar device, but may be used with any ultrasonic energy device such as plastic welders, cell disruptors, surgical handpieces, and dissolution devices for pharmaceuticals.

Figure 2:
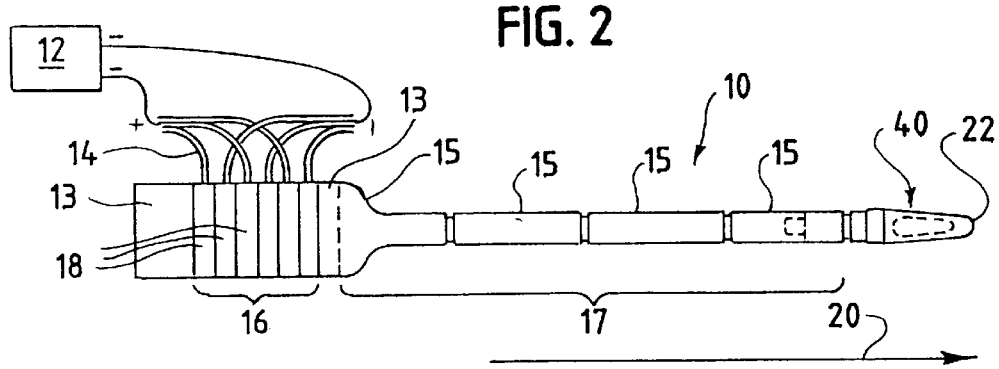
FIG. 2 is a side view of a longitudinal ultrasonic transducer utilizing a hollow tip amplifier made in accordance with the principals of the present invention.

Referring now to FIG. 2, there is shown a longitudinal ultrasonic transducer, generally designated at 10. The transducer 10 includes a power supply 12 which is electrically connected to a generator (not shown) via electrical connectors 14. A longitudinal stack 16 of individual active transduction elements 18 is attached to the power supply 12 in accordance with the ordinary knowledge and skill in the field of ultrasonic transducers. The individual active elements 18 may comprise piezoelectric discs or rings disposed between two non-piezoelectric end masses, such as steel or titanium blocks 13, in a sandwiched configuration. Attached to the stack 16 is a longitudinal stack 17 of half-wave segments 15, and a tip 40 known in the field as a delivery horn is attached to the distal end of the stack 17.

The active elements 18 comprise piezoelement elements such as piezoceramic rings, for example. These active elements 18 are actuated to produce longitudinal waves of ultrasonic energy which propagate through the transducer 10 toward and through the delivery horn 40. The propagation is accomplished when the power supply 12 imparts electrical energy into the stack 16 of piezoelectric elements 18. The energy causes a disturbance in the piezoelectric material in the form of repeated small displacements resulting in large compression and tensile force within the material.

The repeated small displacements within the stack of piezoelectric elements 18 are amplified by exciting the stack 16 and end masses 13 combination to a resonant frequency. The energy is transmitted in the form is the displacements along the half-wave segments 15 to the delivery horn 40. The delivery horn 40 is in contact with a subject to be penetrated (not shown), to thereby deliver the displacement energy to the subject. If desired, some of the half-wave segments 15 may be configured as velocity amplifiers. Otherwise, the segments 15 are "unity gain" segments used to increase the length of the transducer 10.

Figure 1B:
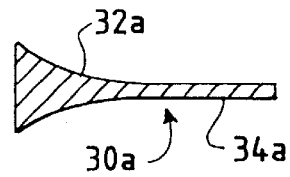
FIG. 1B is a side, cross-section view of another embodiment of a prior art ultrasonic tip amplifier.

The effectiveness of the transducer 10 can be enhanced by amplifying the velocity of the ultrasonic energy, depending upon the geometry of the delivery horn 40. Referring now to FIGS. 1A and 1B, it is known in the prior art to amplify the velocity of the ultrasonic energy waves by attaching a solid, tapering horn 30 or 30a to the distal end of the transducer 10 of FIG. 2.

The prior art tip 30 of FIG. 1A is known in the field as a "traditional stepped horn" because of its larger proximal end 32 and smaller distal end 34. The tip 30 terminates in a distal end 36. The prior art tip 30 has the cross-sectional area reduced simply by the distal end 34 being narrower than the proximal end 32. Some tips have a longitudinal passage 35 formed therein for aspirating the surrounding tissue penetrated by the tip, with the passage 35 terminating in an open distal end 35a. Another prior art tip is shown in FIG. 1B at item 30a. Larger proximal end 32a tapers less abruptly and thus more gradually into smaller distal end 34a.

The prior art horns 30 and 30a are limited because some applications of ultrasonic energy require large cross-sectional areas at the distal delivery end, as opposed to the reduced distal ends 34 or 34a. Additionally, the smaller the tip is, the less blunt it can be generally and thus the easier it is to cause damage, as in the distal end 34a of FIG. 1B.

Figure 3A:
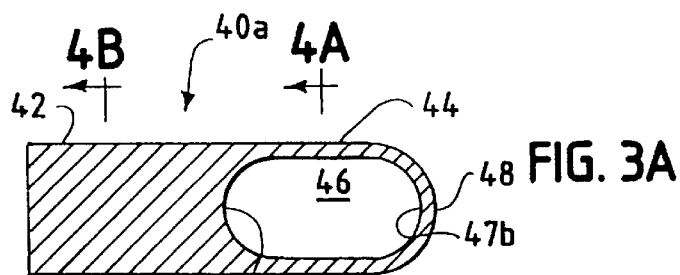
FIG. 3A is a side, cross-sectional view of an ultrasonic tip amplifier made in accordance with the principles of the present invention.

Applicants have conceived of an improved amplification tip, shown generally as a delivery horn 40 in FIG. 2. A preferred embodiment of the delivery horn 40 is shown in FIG. 3A as delivery horn 40a. The horn 40a includes a proximal portion 42 and a hollow distal portion 44. Preferably, the proximal portion 42 is substantially non-hollow. The tip 48 preferably comprises a blunt distal end surface which is preferably characterized by an absence of corners and points as shown in FIG. 3A. The proximal and distal portions 42 and 44 preferably have substantially the same external width in substantially all lateral directions with respect to the length of the horn 40a.

As indicated by the generally designated tip 40 in FIG. 2, the tip is attached to the transducer stack 16 at its distal end. Ultrasonic energy passes from the proximal portion 42 through the distal portion 44 for delivery from the tip 48. The velocity of the ultrasonic energy waves is amplified in proportion to the reduced cross-sectional area of the distal portion 44 relative to the cross-sectional area of the proximal portion 42. However, since the reduction in cross-sectional area of the distal portion 44 is accomplished by an internal cavity or enclosure 46, the external dimensions of the distal portion 44 can be just as large as the proximal portion 42, resulting in a blunter, safer tip. The invention relies on the amplified ultrasonic movement at the tip 48 to improve its tissue-penetrating capacity.

Since the proximal portion 42 is attached to a transducer, the proximal portion 42 receives ultrasonic energy and the energy passes through the distal portion 44 for delivery from the tip 48 to a subject. The delivery horn 40a has a length extending sequentially along the proximal and distal portions 42 and 44. Preferably, the proximal and distal portions 42 and 44 each comprise approximately one-half of the length of the delivery horn 40a, respectively. The delivery horn 40a is preferably configured to receive and transmit ultrasonic energy having a predetermined wavelength, with the length of the delivery horn being substantially equal to one-half of the predetermined wavelength.

Figures 4A, 4B:
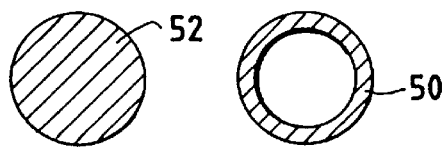
FIG. 4A is a front, cross-sectional view of the amplifier of FIG. 3A, taken along section A—A.
FIG. 4B is a front, cross-sectional view of the amplifier of FIG. 3A, taken along section B—B.

FIG. 4A illustrates a first cross section 50 of the delivery horn 40a taken along section A—A shown in FIG. 3A through the hollow distal portion 44 orthogonal to the length of the horn. Similarly, FIG. 4B illustrates a second cross section 52 taken along section B—B in FIG. 3A, also orthogonally to the horn length. The cross-sectional area of the section 50 is substantially less than the cross-sectional area of the section 52.

Preferably, the cross-sectional area defined by the first cross section 50 is within a range of approximately five percent and ninety-nine percent of the cross-sectional area defined by the second cross section 52. The cross-sectional area of the first section 50 is more preferably less than one-half the cross-sectional area of the second section 52. Most preferably, the cross-sectional area of the first section 50 is approximately thirty-four percent of the cross-sectional area of the second section 52. However, any relative proportion between the sections 50 and 52 may be designed in accordance with a desired magnitude of amplification.

The hollow distal portion 44 defines an internal cavity or enclosure 46 therein which is preferably cylindrical in shape and includes a pair of opposing, rounded ends 47a and 47b, respectively. The enclosure 46 has a width which is preferably greater than one-half of a width of the proximal portion 42. Most preferably, the width of the enclosure is greater than two-thirds of a width of the proximal portion 42.

Figure 3B:
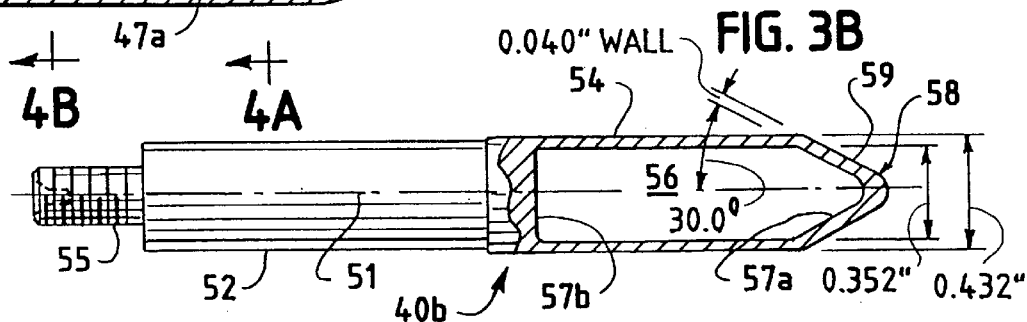
FIG. 3B is a side, partial cross-sectional view of an alternative embodiment of the ultrasonic tip amplifier of FIG. 3A.

An alternative embodiment of the delivery horn 40 of FIG. 2 is shown in FIG. 3B as delivery horn 40b. The delivery horn 40b includes a proximal portion 52 and a hollow distal portion 54. Preferably, the proximal portion 52 is substantially non-hollow. The horn 40b is thus hollow at its distal portion 54, and preferably blunt at its tip 58. The horn 40b also includes an internal cavity or enclosure 56 therein.

Preferably, the enclosure 56 is cylindrical in shape and includes a conical distal end 57a and an opposing end 57b. The distal portion 54 terminates in a continuously radially inwardly tapering exterior distal end 59. The conical distal end 57a of the enclosure 56 and the exterior radial inward taper cooperatively result in distal end 59 having frustoconical sidewalls of substantially uniform wall thickness, and a conical exterior surface. Accordingly, the distal end 59 is defines the distal end 57a of the enclosure 56.

The delivery horn 40 includes means for attaching the proximal portion of the horn to a waveguide shaft, such as the transducer stack 16, as part of an obturator to cause ultrasonic energy transmitted by the waveguide shaft to pass sequentially through the proximal and distal portions, respectively, for delivery from the distal portion to organic tissue as part of an endoscopic surgical procedure. For example, the delivery horn 40b includes attachment insert 55 which is configured for attachment to the transducer stack 16 of FIG. 2.

As indicated in FIG. 3B, the wall thickness of the tip 58 is preferably 0.040 inches, the inner diameter of the hollow distal section 54 is preferably 0.352 inches, and the outer diameter is preferably 0.432 inches. The distal end 59 forms an angle with an axis 51 of the horn 40b of preferably thirty degrees. In the delivery horn 40a of FIG. 3A, the wall thickness of the tip 48 is also preferably 0.040 inches, and the inner and outer diameters of the hollow distal section 44 are also preferably 0.352 inches and 0.432 inches, respectively. However, any desired dimensions and relative proportions of the distal and proximal portions are in accordance with the principles of the present invention.

It is to be understood that the term "hollow" as used herein shall be construed broadly to refer to a delivery horn which defines an enclosure therein, regardless of whether the enclosure is vacant or filled with some other material having a different acoustic impedance than the material of the horn. As long as the delivery horn defines either a vacant enclosure therein capable of measurably amplifying the velocity of ultrasonic energy, or an enclosure filled with material having a different acoustic impedance than the material of the horn, the horn itself is "hollow" as that term is intended herein. It is thus in accordance with the principles of the present invention to provide a hollow delivery horn, such as the horn 40a of FIG. 3A, wherein the enclosure 46 is filled with material having a different acoustic impedance in order to alter the velocity of ultrasonic energy being transmitted through the horn 40a to some predetermined magnitude.

The delivery horns described and claimed herein are used to amplify velocity displacement in ultrasonic energy. This is accomplished through the effect of conservation of energy. As ultrasonic energy is transmitted along a delivery horn having a changing cross-sectional area, ultrasonic energy is conserved and velocity is amplified when the cross-sectional area is reduced. It will be appreciated that if a delivery horn undergoes a fifty percent reduction in cross-sectional area, for example from a proximal to a distal portion of the horn, then the velocity displacement of ultrasonic energy transmitted along that portion of the horn doubles. Conversely, if the cross-sectional area of the horn doubles, then the velocity displacement along that portion of the horn reduces by fifty percent.

Figure 5:
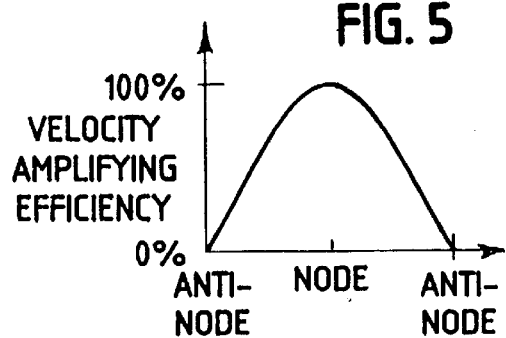
FIG. 5 is a graphical illustration of the efficiency of velocity amplification as the change in cross-sectional area of a delivery horn deviates from a node to an anti-node.

Referring now to FIGS. 3A and 5, it will be appreciated that the efficiency of velocity displacement produced by a delivery horn is a function of the node and anti-node positions on the horn relative to the horn's configuration. For example, it is preferable to design the horn 40a such that the first and second ends 47a and 47b of the enclosure 46 coincide with a node and anti-node, respectively, of the horn 40a, because such an arrangement results in a much higher efficiency of amplification.

The graph in FIG. 5 is intended to illustrate that a step change in cross-sectional area of the horn is theoretically 100% efficient in amplifying velocity of ultrasonic energy transmitted along the horn, if the step change occurs at a node. Conversely, the step change would be 0% efficient if it occurs at an anti-node. Displacement amplitude is increased by introducing cross-sectional changes of the delivery horn 40a at a node, such as by designing the first end 47a of the enclosure 46 to coincide with a node of the horn 40a.

Figure 6A:
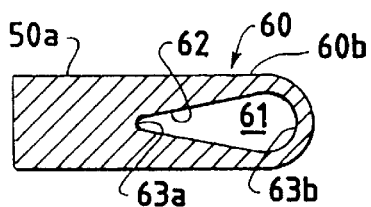
FIG. 6A is a side, cross-sectional view of an alternative embodiment of the ultrasonic tip amplifier of FIG. 3A, involving an internal conical shape.
Figure 6B:
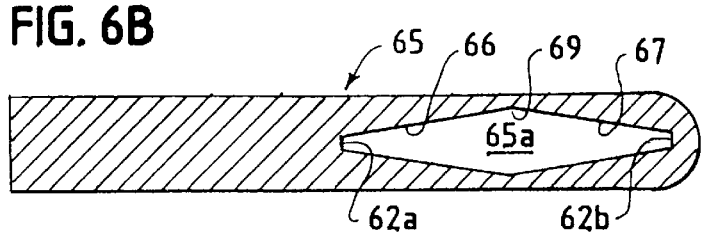
FIG. 6B is a side, cross-sectional view of an alternative embodiment of the ultrasonic tip amplifier of FIG. 6A, involving opposing, co-axial internal conical shapes.

Referring now to FIGS. 6A and 6B, there are shown alternative embodiments of the horn 40a of FIG. 3A. FIG. 6A illustrates a delivery horn 60 having proximal and distal ends 60a and 60b, respectively, An interior surface of the horn 60 defines an enclosure 61. The interior surface includes a conical portion 62 expanding radially outwardly in a proximal to distal direction of the horn 60 as shown. It is to be understood that the term "conical" as used herein shall be construed broadly to refer not only to exterior conical surfaces, but also to exterior frustoconical surfaces, as well as an interior surface such as portion 62 which defines a conical-shaped enclosure. The enclosure 61 includes proximal and distal ends 63a and 63b, preferably positioned to coincide with a node and an anti-node of the horn 60, respectively.

FIG. 6B illustrates a delivery horn 65 which is similar to the delivery horn 60 of FIG. 6A, except that the interior surface defines two opposing conical portions, preferably in a co-axial, symmetrical configuration. A proximal conical portion 66 and a distal conical portion 67 extend sequentially in a proximal to distal direction of the horn 65, defining an enclosure 65a. The term "sequentially" as used herein shall be construed broadly to refer to objects arranged in a certain order, regardless of whether other object not recited reside between the "sequentially" arranged objects. For example, the proximal conical portion 66 and the distal conical portion 67 would extend sequentially in a proximal to distal direction even if a non-conical cylindrical portion resided therebetween.

The enclosure 65a includes proximal and distal ends 68a and 68b, positioned to coincide with a node and an anti-node of the horn 65, respectively. Transition point 69 is the point at which the proximal conical portion 66 and the distal conical portion 67 merge. The transition point 69 preferably coincides with a mid-point between the node and anti-node of the horn 65 which coincide with the proximal and distal enclosure ends 68a and 68b, respectively.

Figure 7A:
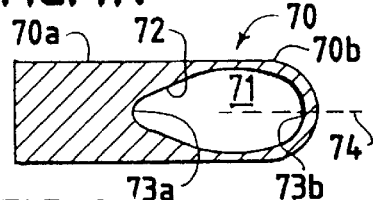
FIG. 7A is a side, cross-sectional view of another alternative embodiment of the ultrasonic tip amplifier of FIG. 3A, involving an interior surface defining exponential curvature.
Figure 7B:
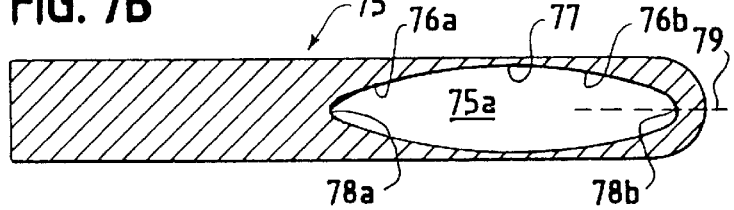
FIG. 7B is a side, cross-sectional view of an alternative embodiment of the ultrasonic tip amplifier of FIG. 7A, involving opposing, co-axial internal shapes of exponential curvature.

Referring now to FIGS. 7A and 7B, there are shown more alternative embodiments of the horn 40a of FIG. 3A. FIG. 7A illustrates a delivery horn 70 having proximal and distal ends 70a and 70b, respectively, An interior surface of the horn 70 defines an enclosure 71. The enclosure 71 includes proximal and distal ends 73a and 73b, preferably positioned to coincide with a node and an anti-node of the horn 70, respectively.

The interior surface includes a concave conical portion 72 expanding radially outwardly in a proximal to distal direction of the horn 70 as shown. The term "conical" as used herein is to be construed broadly to refer to any of the interior surface shapes illustrated in FIGS. 6–10, each of those shapes being generally conical. The more specific phrases "concave conical" and "convex conical" shall refer broadly to conical surfaces having concave and convex portions, respectively. For example, conical surfaces 72 in FIG. 7A and 82a in FIG. 8A are also concave and convex, respectively.

FIG. 7B illustrates a delivery horn 75 which is similar to the delivery horn 70 of FIG. 7A, except that the interior surface defines two opposing concave conical portions, preferably in a co-axial, symmetrical configuration. A proximal concave conical portion 76a and a distal concave conical portion 76b extend sequentially in a proximal to distal direction of the horn 75, defining an enclosure 75a. The enclosure 75a includes proximal and distal ends 78a and 78b, positioned to coincide with a node and an anti-node of the horn 75, respectively. Transition point 77 is the point at which the proximal conical portion 76a and the distal conical portion 76b merge. The transition point 77 preferably coincides with a mid-point between the node and anti-node of the horn 75 which coincide with the proximal and distal enclosure ends 78a and 78b, respectively.

The concave conical portions 72, 76a and 76b preferably define exponential curves, such that at least a portion of a side cross-section of each interior surface shown in FIGS. 7A and 7B defines an exponential profile. Accordingly, each interior surface in FIGS. 7A and 7B also defines an axis 74 and 79, respectively, and preferably extends asymptotically toward a plane extending parallel to those axes 74 and 79. Most preferably, the interior surfaces in FIGS. 7A and 7B extend asymptotically toward a cylindrical boundary (not shown), and in a substantial co-axial orientation with respect to the axes 74 and 79, respectively.

Figure 8A:
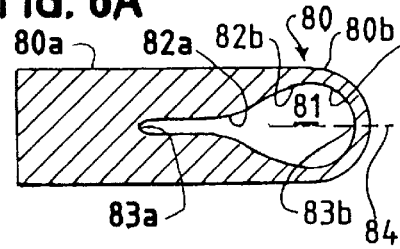
FIG. 8A is a side, cross-sectional view of an additional alternative embodiment of the ultrasonic tip amplifier of FIG. 3A, involving an interior surface defining catenoidal curvature.
Figure 8B:
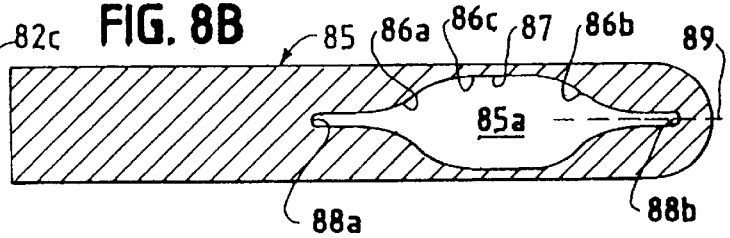
FIG. 8B is a side, cross-sectional view of an alternative embodiment of the ultrasonic tip amplifier of FIG. 8A, involving opposing, co-axial internal shapes of catenoidal curvature.

Referring now to FIGS. 8A and 8B, there are shown additional alternative embodiments of the horn 40a of FIG. 3A. FIG. 8A illustrates a delivery horn 80 having proximal and distal ends 80a and 80b, respectively. An interior surface of the horn 80 defines an enclosure 81. The enclosure 81 includes proximal and distal ends 83a and 83b, preferably positioned to coincide with a node and an anti-node of the horn 80, respectively. The interior surface includes a convex conical portion 82a which merges into a concave conical portion 82b, both of the surface portions 82a and 82b expanding radially outwardly in a proximal to distal direction of the horn 80 as shown.

FIG. 8B illustrates a delivery horn 85 which is similar to the delivery horn 80 of FIG. 8A, except that the interior surface defines two opposing conical portions, preferably in a co-axial, symmetrical configuration. A proximal conical portion 86a and a distal conical portion 86b extend sequentially in a proximal to distal direction of the horn 85. Each of the proximal and distal conical portions 86a and 86b includes a convex conical portion and a concave conical portion as described above in conjunction with FIG. 8A.

The conical portions 86a and 86b define an enclosure 85a of the horn 85. The enclosure 85a includes proximal and distal ends 88a and 88b, positioned to coincide with a node and an anti-node of the horn 85, respectively. Transition point 87 is the point at which the proximal conical portion 86a and the distal conical portion 86b merge. The transition point 87 preferably coincides with a mid-point between the node and anti-node of the horn 85 which coincide with the proximal and distal enclosure ends 88a and 88b, respectively.

The conical portions 82a–b, 86a and 86b preferably define catenoidal curves, such that at least a portion of a side cross-section of each interior surface shown in FIGS. 8A and 8B defines a catenoidal profile. Stated another way, at least a portion of a side cross-section of each of the interior surfaces 82a–b, 86a and 86b defines a catenoidal profile.

In addition, each interior surface portion 82a and 86a in FIGS. 8A and 8B, respectively, extends distally to form a cylindrical portion 82c and 86c, respectively, such that each said surface portion 82a and 86a defines a convex conical portion, concave conical portion and cylindrical portion extending sequentially in a proximal to distal direction of the horn, respectively. Most preferably, each interior surface in FIGS. 8A and 8B extends in a substantial co-axial orientation with respect to axes 84 and 89.

Figure 9A:
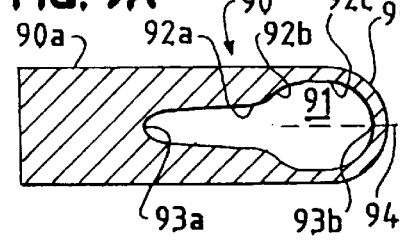
FIG. 9A is a side, cross-sectional view of a further alternative embodiment of the ultrasonic tip amplifier of FIG. 3A, involving an interior surface defining fourier curvature.
Figure 9B:
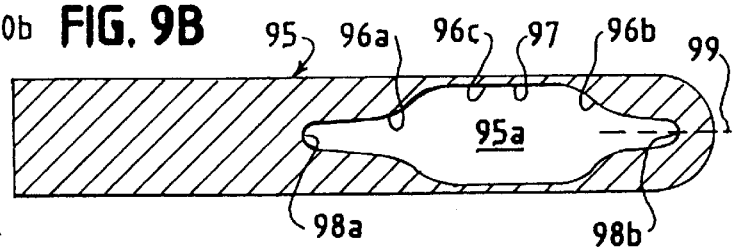
FIG. 9B is a side, cross-sectional view of an alternative embodiment of the ultrasonic tip amplifier of FIG. 9A, involving opposing, co-axial internal shapes of fourier curvature.

Referring now to FIGS. 9A and 9B, there are shown still other alternative embodiments of the horn 40a of FIG. 3A. FIG. 9A illustrates a delivery horn 90 having proximal and distal ends 90a and 90b, respectively. An interior surface of the horn 90 defines an enclosure 91. The enclosure 91 includes proximal and distal ends 93a and 93b, preferably positioned to coincide with a node and an anti-node of the horn 90, respectively. The interior surface includes a convex conical portion 92a which merges into a concave conical portion 92b, both of the surface portions 92a and 92b expanding radially outwardly in a proximal to distal direction of the horn 90 as shown.

FIG. 9B illustrates a delivery horn 95 which is similar to the delivery horn 90 of FIG. 9A, except that the interior surface defines two opposing conical portions, preferably in a co-axial, symmetrical configuration. A proximal conical portion 96a and a distal conical portion 96b extend sequentially in a proximal to distal direction of the horn 95. Each of the proximal and distal conical portions 96a and 96b includes a convex conical portion and a concave conical portion as described above in conjunction with FIG. 9A.

The conical portions 96a and 96b define an enclosure 95a of the horn 95. The enclosure 95a includes proximal and distal ends 98a and 98b, positioned to coincide with a node and an anti-node of the horn 95, respectively. Transition point 97 is the point at which the proximal conical portion 96a and the distal conical portion 96b merge. The transition point 97 preferably coincides with a mid-point between the node and anti-node of the horn 85 which coincide with the proximal and distal enclosure ends 98a and 98b, respectively.

The conical portions 92a–b, 96a and 96b preferably define fourier curves, such that at least a portion of a side cross-section of each interior surface shown in FIGS. 9A and 9B defines a fourier profile. Stated another way, at least a portion of a side cross-section of each of the interior surfaces 92a–b, 96a and 96b defines a fourier profile.

In addition, each interior surface portion 92a and 96a in FIGS. 9A and 9B, respectively, extends distally to form a cylindrical portion 92c and 96c, respectively, such that each said surface portion 92a and 96a defines a convex conical portion, concave conical portion and cylindrical portion extending sequentially in a proximal to distal direction of the horn, respectively. Most preferably, each interior surface in FIGS. 9A and 9B extends in a substantial co-axial orientation with respect to axes 94 and 99.

Figure 10A:
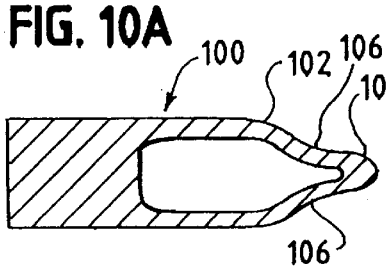
FIG. 10A is a side, cross-sectional view of still another alternative embodiment of the ultrasonic tip amplifier of FIG. 3A, including external facets formed therein.
Figure 10B:
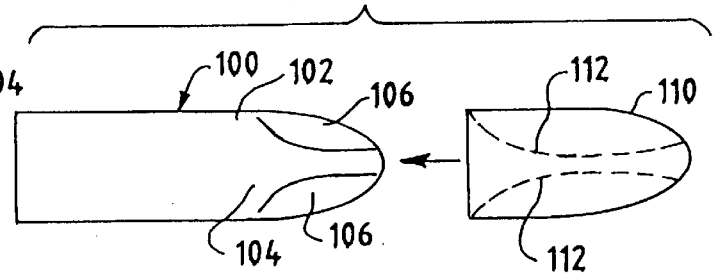
FIG. 10B is a side, exterior view of the ultrasonic tip amplifier of FIG. 10A, shown in conjunction with a protective cap.
Figure 10C:
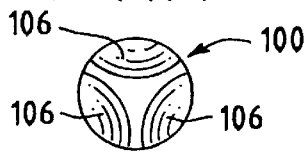
FIG. 10C is a front view of the ultrasonic tip amplifier of FIG. 10B.

Referring now to FIGS. 10A, 10B and 10C, there is shown a faceted delivery horn 100. A distal portion 102 of the horn 100 comprises an exterior surface 104 having a plurality of concave recesses 106 formed therein. The distal portion 102 is thereby configured and dimensioned to receive a protective covering 110 (FIG. 10B) thereon having a plurality of mating surfaces 112 for engagement within the concave recesses. Preferably, the concave recesses 106 comprise three facets of substantially equivalent size and shape positioned around the distal portion of the horn 100.

In accordance with the disclosure set forth above, a preferred method for amplifying velocity of ultrasonic energy comprises the steps of:

(a) selecting a delivery horn having a solid proximal portion and a hollow distal portion, said hollow distal portion having less cross-sectional area than the solid proximal portion; and (b) transmitting ultrasonic energy sequentially through the proximal and distal portions, respectively, of the delivery horn to amplify the velocity of the ultrasonic energy as said energy passes from said hollow distal portion.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. An ultrasonic energy amplifier comprising:
a delivery horn having a proximal portion for receiving ultrasonic energy and a distal portion through which the ultrasonic energy is delivered, said distal portion being hollow in the form of an enclosure to amplify the velocity of the ultrasonic energy as said energy is delivered through said hollow distal portion.

2. The ultrasonic energy amplifier as defined in claim 1, wherein the delivery horn has a length extending sequentially along the proximal and distal portions, respectively, said proximal and distal portions each comprising approximately one-half of said length, respectively, said proximal portion being substantially non-hollow.

3. The ultrasonic energy amplifier as defined in claim 1, wherein the delivery horn has a length extending sequentially along the proximal and distal portions, respectively, and wherein a first cross section of the delivery horn taken through the hollow distal portion orthogonal to the length of the horn defines a cross-sectional area which is less than a cross-sectional area defined by a second cross section taken orthogonally through the proximal portion of the delivery horn.

4. The ultrasonic energy amplifier as defined in claim 3, wherein the cross-sectional area defined by the first cross section is less than one-half the cross-sectional area defined by the second cross section.

5. The ultrasonic energy amplifier as defined in claim 3, wherein the cross-sectional area defined by the first cross section is within a range of approximately five percent and ninety-nine percent of the cross-sectional area defined by the second cross section.

6. The ultrasonic energy amplifier as defined in claim 5, wherein the cross-sectional area defined by the first cross section is approximately thirty-four percent of the cross-sectional area defined by the second cross section.

7. The ultrasonic energy amplifier as defined in claim 1, wherein the hollow distal portion of the delivery horn defines an enclosure therein which is cylindrical in shape and includes a pair of opposing, rounded ends.

8. The ultrasonic energy amplifier as defined in claim 1, wherein the hollow distal portion of the delivery horn defines an enclosure therein having a width which is greater than one-half of a width of the proximal portion, both of said widths being measured along a common plane.

9. The ultrasonic energy amplifier as defined in claim 1, wherein the hollow distal portion of the delivery horn defines an enclosure therein having a width which is greater than two-thirds of a width of the proximal portion, both of said widths being measured along a common plane.

10. The ultrasonic energy amplifier as defined in claim 1, wherein the delivery horn terminates in a blunt distal end surface, said surface being characterized by an absence of corners and points.

11. The ultrasonic energy amplifier as defined in claim 1, wherein the hollow distal portion of the delivery horn defines an enclosure therein which is cylindrical in shape and includes a conical distal end.

12. The ultrasonic energy amplifier as defined in claim 1, wherein the delivery horn has a length extending sequentially along the proximal and distal portions, respectively, and terminates in a continuously radially-inwardly-tapering tapering distal end.

13. The ultrasonic energy amplifier as defined in claim 12, wherein the radially-inwardly-tapering distal end comprises a conical exterior surface.

14. The ultrasonic energy amplifier as defined in claim 12, wherein the hollow distal portion of the delivery horn defines an enclosure having a distal end, and wherein the tapering distal end of the delivery horn comprises a distal end wall which defines the distal end of the enclosure and which is substantially uniform in thickness.

15. The ultrasonic energy amplifier as defined in claim 1, wherein the delivery horn includes means for attaching the proximal portion of the horn to a waveguide shaft as part of an obturator to cause ultrasonic energy transmitted by said waveguide shaft to pass sequentially through the proximal and distal portions, respectively, for delivery from the distal portion to organic tissue as part of an endoscopic surgical procedure.

16. The ultrasonic energy amplifier as defined in claim 1, wherein the delivery horn is configured to receive and transmit ultrasonic energy having a predetermined wavelength, said delivery horn having a length which is substantially equal to one-half of said predetermined wavelength.

17. The ultrasonic energy amplifier as defined in claim 1, wherein the horn has a length and wherein the proximal and distal portions of the delivery horn each have substantially the same external width in substantially all lateral directions with respect to the length of the horn.

18. The ultrasonic energy amplifier as defined in claim 1, wherein the hollow distal portion defines an enclosure therein having proximal and distal ends positioned to coincide with a node and an anti-node of the horn, respectively.

19. The ultrasonic energy amplifier as defined in claim 1, wherein the hollow distal portion of the delivery horn includes an interior surface defining an enclosure, said interior surface having a conical portion expanding radially outwardly in a proximal to distal direction of the horn.

20. The ultrasonic energy amplifier as defined in claim 19, wherein the enclosure defined by the interior surface includes proximal and distal ends positioned to coincide with a node and an anti-node of the horn, respectively.

21. The ultrasonic energy amplifier as defined in claim 19, wherein the enclosure defined by the interior surface comprises a proximal conical portion and a distal conical portion, said conical portions extending sequentially in a proximal to distal direction of the horn and being disposed in a substantial co-axial orientation relative to one another.

22. The ultrasonic energy amplifier as defined in claim 1, wherein the hollow distal portion of the delivery horn includes an interior surface defining an enclosure, said interior surface having a concave conical portion expanding radially outwardly in a proximal to distal direction of the horn.

23. The ultrasonic energy amplifier as defined in claim 22, wherein the enclosure defined by the interior surface includes proximal and distal ends positioned to coincide with a node and an anti-node of the horn, respectively.

24. The ultrasonic energy amplifier as defined in claim 22, wherein the enclosure defined by the interior surface comprises a proximal concave conical portion and a distal concave conical portion, said conical portions extending sequentially in a proximal to distal direction of the horn and being disposed in a substantial co-axial orientation relative to one another.

25. The ultrasonic energy amplifier as defined in claim 22, wherein the concave conical portion of the interior surface defines an axis and extends asymptotically toward a plane extending parallel to said axis.

26. The ultrasonic energy amplifier as defined in claim 22, wherein the concave conical portion of the interior surface defines an axis and extends asymptotically toward a cylindrical boundary extending in a substantial co-axial orientation with respect to said axis.

27. The ultrasonic energy amplifier as defined in claim 22, wherein at least a portion of a side cross-section of the interior surface defines an exponential profile.

28. The ultrasonic energy amplifier as defined in claim 1, wherein the hollow distal portion of the delivery horn includes an interior surface defining an enclosure, said interior surface comprising a convex conical portion expanding radially outwardly in a proximal to distal direction of the horn.

29. The ultrasonic energy amplifier as defined in claim 28, wherein the enclosure defined by the interior surface includes proximal and distal ends positioned to coincide with a node and an anti-node of the horn, respectively.

30. The ultrasonic energy amplifier as defined in claim 28, wherein the enclosure defined by the interior surface comprises a proximal convex conical portion and a distal convex conical portion, said conical portions extending sequentially in a proximal to distal direction of the horn and being disposed in a substantial co-axial orientation relative to one another.

31. The ultrasonic energy amplifier as defined in claim 28, wherein the interior surface comprises, in addition to the convex conical portion, a concave conical portion and a cylindrical portion, such that said convex conical portion, concave conical portion and cylindrical portion extend sequentially in a proximal to distal direction of the horn, respectively.

32. The ultrasonic energy amplifier as defined in claim 28, wherein at least a portion of a side cross-section of the interior surface defines a catenoidal profile.

33. The ultrasonic energy amplifier as defined in claim 28, wherein at least a portion of a side cross-section of the interior surface defines a fourier profile.

34. The ultrasonic energy amplifier as defined in claim 1, wherein the distal portion of the delivery horn comprises an exterior surface having a plurality of concave recesses formed therein such that said distal portion is configured and dimensioned to receive a protective covering thereon having a plurality of mating surfaces for engagement within the concave recesses.

35. The ultrasonic energy amplifier as defined in claim 34, wherein the plurality of concave recesses comprises three facets of substantially equivalent size and shape positioned around the distal portion of the horn.

36. An ultrasonic energy amplifier comprising:
a delivery horn having a proximal portion and a distal portion, said delivery horn being configured for receiving ultrasonic energy at said proximal portion and channeling said energy sequentially through said proximal and distal portions, respectively, such that said energy is delivered from the distal portion, said distal portion having a hollow enclosure formed therein sufficient in size to amplify the velocity of the ultrasonic energy as said energy is delivered through said distal portion.

37. A method for amplifying velocity of ultrasonic energy, said method comprising the steps of:
(a) selecting a delivery horn having a solid proximal portion and a hollow enclosure distal portion, said hollow distal portion having less cross-sectional area than the solid proximal portion; and
(b) transmitting ultrasonic energy sequentially through the proximal and distal portions, respectively, of the delivery horn to amplify the velocity of the ultrasonic energy as said energy passes from said hollow distal portion.

38. An ultrasonic energy amplifier comprising:
a delivery horn having a proximal portion and a hollow enclosure distal portion, the hollow distal portion terminating in an inwardly-tapering distal end and a cross-sectional area which is less than a cross-sectional area of the proximal portion.

* * * * *